(12) United States Patent
Nagae

(10) Patent No.: US 10,295,509 B2
(45) Date of Patent: May 21, 2019

(54) ULTRASONIC APPARATUS

(71) Applicant: CANON KABUSHIKI KAISHA, Tokyo (JP)

(72) Inventor: Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 437 days.

(21) Appl. No.: 14/791,585

(22) Filed: Jul. 6, 2015

(65) Prior Publication Data

US 2015/0308985 A1 Oct. 29, 2015

Related U.S. Application Data

(63) Continuation of application No. 13/147,963, filed as application No. PCT/JP2010/001278 on Feb. 25, 2010, now Pat. No. 9,110,155.

(30) Foreign Application Priority Data

Mar. 3, 2009 (JP) ................................. 2009-048746

(51) Int. Cl.
   *G01F 7/00* (2006.01)
   *G01N 29/44* (2006.01)
   *G01S 7/52* (2006.01)

(52) U.S. Cl.
   CPC .......... *G01N 29/44* (2013.01); *G01S 7/52047* (2013.01); *G01N 2291/106* (2013.01)

(58) Field of Classification Search
   CPC .............. G01N 29/44; G01N 2291/106; G01S 7/52047

(Continued)

(56) References Cited

U.S. PATENT DOCUMENTS 6,154,552 A * 11/2000 Koroljow .............. G01S 3/8006
                                                        367/119
8,761,477 B2 * 6/2014 Walker ................ G01S 7/52026
                                                        370/342

(Continued)

FOREIGN PATENT DOCUMENTS

| JP | S59-049751 | 3/1984 |
|----|------------|--------|
| JP | H2-209135  | 8/1990 |
| JP | 2007-024660 | 2/2007 |

OTHER PUBLICATIONS

Takao et al., "An Adaptive Antenna Array Under Directional Constraint", *IEEE Transactions on Antennas and Propagation*, vol. AP-24, No. 5, pp. 662-669, (Sep. 1976), XP002555749.

(Continued)

*Primary Examiner* — Toan M Le
*Assistant Examiner* — Xiuqin Sun
(74) *Attorney, Agent, or Firm* — Venable LLP

(57) ABSTRACT

An ultrasonic apparatus is provided with an adaptive signal processing block (007) and a fixed signal processing block (006). The adaptive signal processing block generates a first intermediate signal by calculating a correlation matrix of a plurality of received electrical signals, extracting a plurality of sub-matrices from the correlation matrix, calculating a sub-correlation matrix by averaging the plurality of sub-matrices, determining a weighting coefficient from the sub-correlation matrix, and synthesizing the plurality of received electrical signals by using the weighting coefficient. The fixed signal processing block generates a second intermediate signal by synthesizing the plurality of received electrical signals with the use of a predetermined weighting coefficient. Then, a comparison and synthesis processing block (Continued)

(008) generate an output signal by comparing and synthesizing the first and second intermediate signals with each other.

26 Claims, 10 Drawing Sheets

(58) Field of Classification Search
USPC .......................................................... 702/56
See application file for complete search history.

(56) References Cited

U.S. PATENT DOCUMENTS

| 2008/0306371 A1 | 12/2008 | Fukutani et al. ............. 600/407 |
| 2009/0005685 A1 | 1/2009 | Nagae et al. ................. 600/459 |
| 2009/0275837 A1 | 11/2009 | Shiina et al. ................. 600/459 |
| 2009/0299185 A1 | 12/2009 | Oikawa et al. .............. 600/447 |
| 2011/0083511 A1 | 4/2011 | Taki et al. ....................... 73/602 |
| 2011/0208035 A1 | 8/2011 | Baba et al. ................... 600/407 |
| 2012/0044785 A1 | 2/2012 | Yoda et al. ..................... 367/92 |

OTHER PUBLICATIONS

Sasso et al., "Medical Ultrasound Imaging Usinq the Fully Adaptive Beamformer", *2005 IEEE International Conference on Acoustics, Speech, and Signal Processing*, vol. 2, pp. 489-492 (2005), XP010790683.

Park et al., "Adaptive Beamforming for Photoacoustic Imaging", *Optics Letters*, Optical Society of America, vol. 33, No. 12, pp. 1291-1293 (Jun. 2008), XP001514307.

Shan et. al., "Adaptive Beamforming for Coherehnt Signals and Interference", *IEEE Transactions Acoustics, Speech, and Signal Processing*, vol. ASSP-33, No. 3, pp. 527-536 (Jun. 1985), XP002585452.

Synnevåg et al., "Adaptive Beamforming Applied to Medical Ultrasound Imaging", *IEEE Transactions on Ultrasonics, Ferroelectrics, and Frequency Control*, vol. 54, No. 8, pp. 1606-1161 (Aug. 2007), XP011190325.

Synnevåg et al., "Minimum Variance Adaptive Beamforming Applied to Medical Ultrasound Imaging", 2005 Ultrasonics Symposium, vol. 2, pp. 1199-1202 (Sep. 2005), XP010899040.

Park et al., "Adaptive Beamforming for Photoacoustic Imaging Using Linear Array Transducer", *2008 IEEE International Ultrasonics Symposium Proc.*, pp. 1088-1091 (Nov. 2008), XP031443268.

Holfort et al., "Plane Wave Medical Ultrasound Imaging Using Adaptive Beamforming", *Sensor Array and Multichannel Signal Processing Workshop*, pp. 288-292 (Jul. 2008), XP031312336.

Viola et al., "Adaptive Signal Processing in Medical Ultrasound Beamforming", *2005 IEEE Ultrasonics Symposium*, vol. 4, pp. 1980-1983 (Sep. 2005), XP0108991852005.

\* cited by examiner

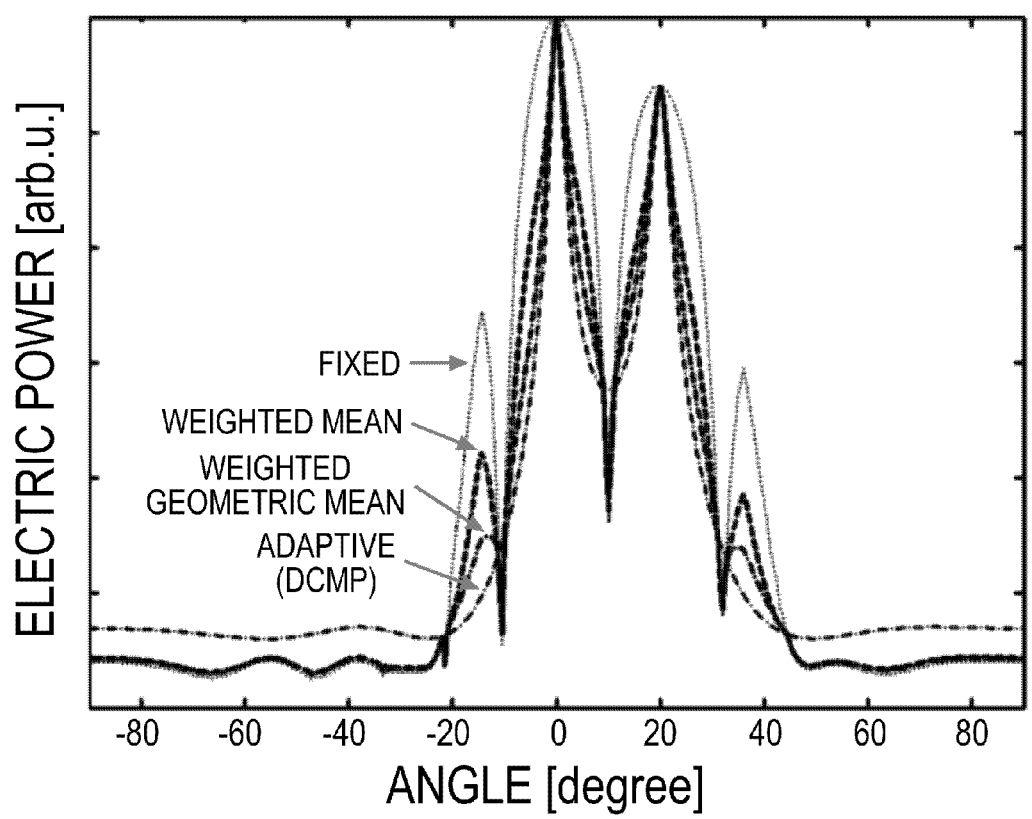

ULTRASONIC APPARATUS

RELATED APPLICATIONS

This is a continuation of application Ser. No. 13/147,963, filed Aug. 4, 2011, which is a national-stage entry of International Application PCT/JP2010/001278. It claims benefit of that application number under 35 U.S.C. § 120, and claims benefit under 35 U.S.C. § 119 of Japanese patent application no. 2009-48746, filed on Mar. 3, 2009. The entire contents of each of the mentioned prior applications are incorporated herein by reference.

TECHNICAL FIELD

The present invention relates to an ultrasonic apparatus which acquires biological information using an ultrasonic signal received from a specimen, and in particular, it relates to an ultrasonic apparatus which performs adaptive signal processing on a received signal.

BACKGROUND ART

As a technique to acquire biological information (e.g., a tomographic image or a three-dimensional image) in a specimen by receiving an ultrasonic wave from the interior of the specimen, there has been an ultrasonic echo, photoacoustic tomography (PAT), and so on. The ultrasonic echo is a method of transmitting an ultrasonic wave to a specimen and receiving its reflected wave. The photoacoustic tomography is a method of transmitting optical energy to the interior of a specimen and receiving an elastic wave (ultrasonic wave) produced as a result of the adiabatic expansion of the specimen due to absorption of the optical energy.

On the other hand, there is also adaptive signal processing which has been developed in the field of radar, etc. A directionally constrained minimization of power (DCMP), being one of adaptive signal processing schemes, is a technique in which when signals are received by a plurality of elements, the plurality of signals thus received are operation processed so as to minimize signal power with the sensitivity in a certain direction (e.g., a direction in which one wants to obtain a signal) being fixed. In adaptive signal processing, a processing parameter for each received signal is adaptively changed (Non Patent Literature (NPL) 1). Such adaptive signal processing is effective in improving spatial resolution, in particular the resolution in the azimuth direction. NPL 2 describes the result of improved resolution obtained by combining such adaptive signal processing with an ultrasonic wave, and NPL 3 describes the result of imaging obtained by combining adaptive signal processing with photoacoustics. As described in NPL 2 and NPL 3, a correlation matrix is first calculated from received signals, and sub-matrices are then extracted therefrom, so that adaptive processing is carried out by the use of a sub-correlation matrix obtained by averaging them. This is a technique shown as spatial smoothing in NPL 4.

In the following, the processing of the DCMP will be described, and then the necessity of using spatial smoothing will be described.

It is assumed that signals have been received by an array having K receiving elements. A signal received by the k-th element is set as $x_k(t)$. In this case, a signal group received by the K elements can be denoted by $X(t)$. Here, note that signals are all analytical expressions.

$$X(t)=[x_1(t),x_2(t),\ldots,x_K(t)]^T$$

Here, note that a superscript "T" means a transposition. In order to synthesize these signals to generate an output, received signals are multiplied by a complex weight vector W.

$$W=[w_1,w_2,\ldots,w_K]^T$$

By this, an output y(t) is obtained.

$$y(t)=W^H X(t)=X^T(t)W^*$$

Here, note that a superscript "H" means a complex conjugate transposition, and a superscript "*" means a complex conjugate.

By changing this complex weight vector to an optimal one according to input signals, an output y is obtained which has been subjected to signal processing in an adaptive manner.

In order to calculate an optimal complex weight vector, a correlation matrix is first calculated based on input signals as follows.

$$R_{xx}=E[X(t)X^H(t)]$$

Here, $E[\cdot]$ means calculating a time average.

In such a state, W under the following conditions is calculated.

$$\min_W(W^H R_{xx} W)$$

$$\text{subject to } W^H a = 1$$

These conditions mean minimizing output power with a sensitivity in a desired direction (a direction in which one wants to obtain a signal) being fixed. Here, note that "a" is a steering vector and specifies the desired direction.

When an optimum weight Wopt is calculated under such conditions, the following result is obtained.

$$Wopt = \frac{R_{xx}^{-1} a}{a^H R_{xx}^{-1} a}$$

By using this optimum weight, the output power can be minimized with the sensitivity in the desired direction being set to 1. That is, a receiving array using this optimum weight forms a receiving pattern having such a directivity that the sensitivity in the desired direction is set to 1 and the sensitivity in the directions of arrival of noise components is low. In addition, electric power Pout from the desired direction can be expressed as follows.

$$Pout = \frac{1}{2a^H R_{xx}^{-1} a}$$

The above description until this point states the basic principle of the DCMP.

However, the above-mentioned principle is materialized in cases where a noise component and a desired wave do not have correlativity, but not in cases where a noise component and a desired wave have correlativity. Specifically, in cases where a noise component having correlativity with a desired wave is received, a directive receiving pattern is formed which has a sensitivity of 1 in the direction of the desired wave but a sensitivity in the direction of the noise component at an opposite phase, too. This is because a signal to be output is made near zero so as to minimize the output signal by adding the noise component to the desired wave at the opposite phase.

Incidentally, in cases where imaging is carried out by making use of the transmission and reception of an ultrasonic wave or a photoacoustic effect, a noise component coming in (arriving at) from other than a desired direction has high correlativity with a desired component. This is because in imaging by an ultrasonic wave, the imaging is carried out by the use of reflected waves of an ultrasonic wave that has been transmitted from the element array in order to obtain image information, so a reflected wave from a desired direction and reflected waves reflected from directions other than the desired direction have high correlation. In addition, in imaging by making use of a photoacoustic effect, too, incident light spreads to a wide area due to a scattering effect. Then, in cases where generating causes (absorbers, etc.) for photoacoustic waves of high correlativity (similarity) exist in a specimen, ultrasonic waves generated from such a wide area have a high possibility that they have high correlativity with one another.

A technique that enables the DCMP to operate also on such noise of high correlativity is a spatial smoothing. The spatial smoothing calculates an optimum weight by extracting a plurality of sub-matrices from a correlative matrix as referred to above, and using a sub-correlation matrix which is calculated from an average of the sub-matrices.

A sub-correlation matrix Rpxx can be calculated by the following formulae.

$$X_n(t) = [x_n(t), x_{n+1}(t), \ldots , x_{n+M-1}(t)]^T \ (n = 1, 2, \ldots , N)$$

$$R_{pxx} = \sum_{n=1}^{N} z_n E[X_n(t) \ X_n^H(t)]$$

Here, note that N is the number of sub-matrices to be extracted, and M is the size of a sub-matrix obtained at K−N+1. In addition, Zn is a weighting coefficient at the time of averaging the sub-matrices, and the averaging becomes a simple mean at the time of Zn=1/N, but it is also possible to use, as a weighting function, a Hamming window, a Hanning window, a Dolph-Chebycheff window, etc.

By calculating the optimum weight with the use of the sub-correlation matrices Rpxx as mentioned above, it is possible to avoid having sensitivity in the direction of a noise component even if the noise component having high correlativity with a desired wave is received. Therefore, even in cases where an ultrasonic wave is used for transmission and reception, or in the case of imaging by making use of a photoacoustic effect, it becomes possible to obtain the effect due to the DCMP, i.e., the effect of an improvement in the spatial resolution in azimuth direction.

Here, note that Patent Literature (PTL) 1 discloses an apparatus that divides a receiving aperture into sub-apertures, and selects a datum of the smallest output from among those data which have been received at the sub-apertures, respectively, and subjected to similar signal processing.

(PTL 1) Japanese patent application laid-open No. H02-209135
(NPL 1) IEEE Trans. Antennas & Propag. Vol. AP-24, No. 5, pp. 662-669 (September 1976)
(NPL 2) Proc. Acoustics, Speech Signal Process, pp. 489-492 (March 2005)
(NPL 3) OPTICS LETTERS, Vol. 33, No. 12, pp 1291-1293 (Jun. 15, 2008)
(NPL 4) IEEE Trans. Acoust, Speech, Signal Process, Vol. ASSP-33, No. 3, pp. 527-536 (June 1985)

SUMMARY OF INVENTION

As described above, by using spatial smoothing, it become possible to perform adaptive signal processing even in cases where an ultrasonic wave is used for transmission and reception, or in the case of imaging by making use of a photoacoustic effect. However, the present inventors have found out that a new problem arises when using spatial smoothing.

Now, the problem will be described below while illustrating the result of a simulation actually processed by the DCMP. FIG. 8A plots arrival electric power at each given angle in cases where signals come to a receiving array with 11 elements from directions of 0 degrees and 20 degrees with respect thereto, respectively. A fixed type (Boxcar) is the result of processing with a weight vector being fixed so as to become a uniform magnitude, and a fixed type (Hamming) is the result of processing with a weight vector being fixed as a coefficient for a Hamming window. In addition, an adaptive type (DCMP) is the result of processing by using spatial smoothing. The size of a sub-matrix was set to 5. The axis of abscissa in this figure represents angle, and the axis of ordinate represents the electric power of incoming or arrival signals.

It can be seen that in either of the processing techniques, signals come from a direction of 0 degrees and a direction of 20 degrees, respectively. In particular, the result of processing by the adaptive type (DCMP) is that the azimuth resolution is high and the electric power in directions other than the directions of arrival of the signals is suppressed to a low level. In addition, in the techniques such as the fixed type (Boxcar) and the fixed type (Hamming), the convolution of the directivity of a receiving pattern formed by a receiving array and signal position is plotted as arrival electric power. In the fixed type, peaks produced in directions different from the arrival directions reflect side lobes 101, 102 of receiving patterns, respectively.

Then, the directivity of a receiving pattern formed by each technique is considered. FIG. 8B plots array response values formed by the above-mentioned three kinds of techniques at the time when the receiving direction is constrained to 0 degrees, and shows the directivity of each receiving pattern. In the fixed type (Boxcar) and the fixed type (Hamming), directivity patterns are fixed by the positions of elements and a fixed weight. It can be seen that a main lobe width 201 of the fixed type (Hamming) is wider than that of the fixed type (Boxcar), but a side lobe level of the fixed type (Hamming) is lower than that of the fixed type (Boxcar). In addition, when focusing on the adaptive type (DCMP), it can be seen that a low sensitivity portion null 202 is formed in a direction of 20 degrees, and signals from other than the desired direction (0 degrees) are suppressed. However, it can also be seen that a main lobe width 203 of the adaptive type (DCMP) is wider than that of the other fixed types, and the side lobe level thereof is higher.

That is, in the processing of the adaptive type, at the time when the intensities of signals in the directions of arrival thereof are plotted, the azimuth resolution is also high and the side lobe level is also low, but the directivity of the actual receiving pattern is wide in the main lobe and is high in the side lobe level. This is because the substantial size of a receiving aperture becomes smaller due to the use of spatial smoothing, and a degree of freedom for suppression of noise components oppression is used by spatial smoothing.

In the examples described so far, although the deterioration of the receiving pattern is seen due to the use of spatial smoothing, the final result, i.e., arrival electric power at each given angle, is that the processing of the adaptive type is the most preferable among the three kinds of processing.

Subsequently, FIG. 8C plots arrival electric power at each given angle when noise in the background increases. When the three kinds of processing techniques are compared with one another, the azimuth resolution of the adaptive type (DCMP) is the highest, but the side lobe level thereof is higher than those of the fixed type (Boxcar) and the fixed type (Hamming), and the arrival electric power thereof in the direction of 10 degrees is higher than that of the fixed type (Boxcar). This means that in cases where noise in the background increases, because in the adaptive type processing, the main lobe of the receiving pattern is wide or the received side lobe level is high, the side lobe level of the arrival electric power may become higher in the adaptive type processing as compared with that in the fixed type. Thus, in cases where the signal processing of the adaptive type using spatial smoothing is carried out, the side lobe level may become high depending on the condition of a received signal, thereby giving rise to a problem that the contrast ratio of an image decreases.

The present invention is made in view of the above-mentioned problem, and has for its object to provide an ultrasonic apparatus which is high in azimuth resolution and is also good in the contrast ratio of an image.

The present invention provides an ultrasonic apparatus which acquires biological information by using an ultrasonic signal received from a specimen, the apparatus comprising: a plurality of transducers that receive ultrasonic signals and convert them into received electrical signals, respectively; an adaptive signal processing unit that generates a first intermediate signal by calculating a correlation matrix of the plurality of received electrical signals obtained from the plurality of transducers, extracting a plurality of sub-matrices from the correlation matrix, calculating a sub-correlation matrix by averaging the plurality of sub-matrices, determining a weighting coefficient from the sub-correlation matrix, and synthesizing the plurality of received electrical signals with the use of the weighting coefficient; a fixed signal processing unit that generates a second intermediate signal by synthesizing the plurality of received electrical signals with the use of a predetermined weighting coefficient; and a synthesizing unit that generates an output signal to be used for construction of the biological information by synthesizing the first intermediate signal and the second intermediate signal through a comparison therebetween.

According to the present invention, it is possible to provide an ultrasonic apparatus which is high in azimuth resolution and is also good in the contrast ratio of an image.

Further features of the present invention will become apparent from the following description of exemplary embodiments with reference to the attached drawings.

BRIEF DESCRIPTION OF DRAWINGS

FIG. 7B is a view explaining the effect thereof.

DESCRIPTION OF EMBODIMENTS

Figure 1:
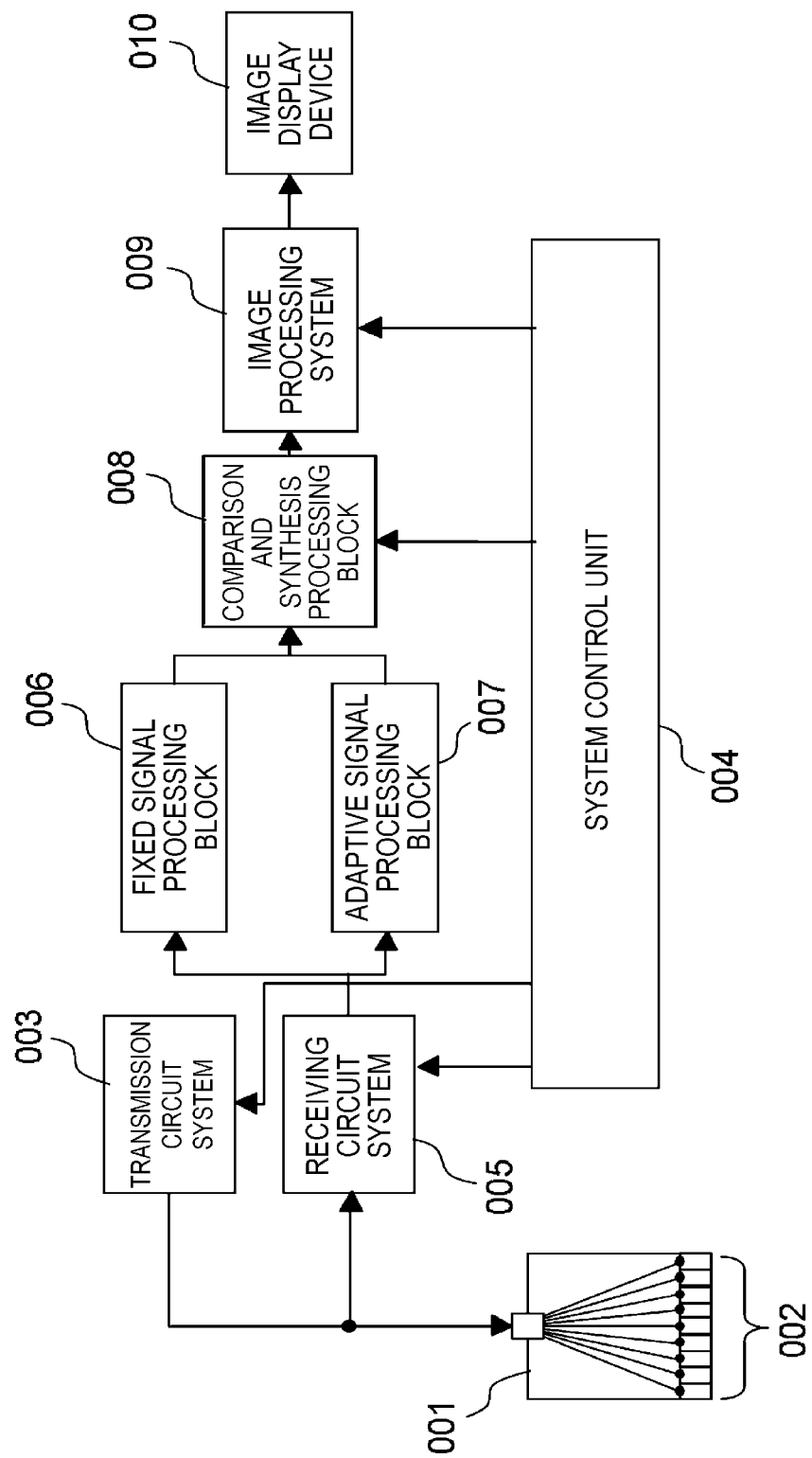
FIG. 1 is a block diagram of an ultrasonic apparatus.

Hereinafter, preferred embodiments of this invention will be described in detail by way of example with reference to the attached drawings. An ultrasonic apparatus according to the present invention is an apparatus that acquires biological information (a tomographic image, a three-dimensional image, etc.) by using an ultrasonic signal (an elastic wave signal) received from a specimen. This apparatus is used for medical ultrasonic diagnosis, for example. A characteristic construction of the present invention resides in that with respect to received signal processing (forming of a received beam) of an ultrasonic wave, a result of adaptive signal processing (a first intermediate signal) and a result of fixed signal processing (a second intermediate signal) are synthesized to produce an output signal that is used for the construction of biological information. By constructing an image from this output signal, an improvement in azimuth resolution and an improvement in the contrast ratio of the image are achieved. The adaptive signal processing is a method of adaptively changing a weighting coefficient (weight vector) at the time of synthesizing received electrical signals obtained by a plurality of transducers in accordance with the signals in order to improve the sensitivity in a desired observation direction. A directionally constrained minimization of power (DCMP), for example, can be preferably used as adaptive signal processing. Moreover, other adaptive signal processing such as a least mean squared error algorithm (LMS), a maximum S/N (MSN), and a MUSIC (Multiple Signal Classification) method, etc., can also be used. In addition, it is preferable to combine so-called spatial smoothing with adaptive signal processing for the purpose of controlling or suppressing the correlativity between a desired wave and noise. The spatial smoothing is a method of calculating a correlation matrix of received electrical signals, extracting a plurality of sub-matrices from the correlation matrix, calculating a sub-correlation matrix by averaging the plurality of sub-matrices, and determining a weighting coefficient from the sub-correlation matrix. On the other hand, the fixed signal processing is a method of synthesizing a plurality of received electrical signals by using a predetermined (fixed) weighting coefficient. As the fixed signal processing, there are a method of setting a weighting coefficient to a uniform magnitude (called a fixed type (Boxcar)), a method of setting a weighting coefficient as a coefficient of a Hamming window (called a fixed type (Hamming)), and so on. Here, note that anything can be used as a window function (weighing function) of the weighting coefficient. Hereinafter, reference will be made to a specific technique of synthesizing the first and second intermediate signals.

First Embodiment

In a first embodiment, reference will be made to an ultrasonic apparatus that carries out processing by using of signal power.

(Construction of the Ultrasonic Apparatus)

FIG. 1 is a system outline view of the ultrasonic apparatus. The ultrasonic apparatus is provided with an ultrasonic probe 001, a transmission circuit system 003, a system control unit 004, a receiving circuit system 005, a fixed signal processing block 006, an adaptive signal processing block 007, a comparison and synthesis processing block 008, and an image processing system 009. The ultrasonic probe 001 is provided with a plurality of transducers 002. An image display device 010 for displaying an image outputted from the image processing system 009 is connected to this ultrasonic apparatus. The adaptive signal processing block 007 is an adaptive signal processing unit which generates a first intermediate signal from a received electrical signal by means of a DCMP while applying spatial smoothing thereto. The fixed signal processing block 006 is a fixed signal processing unit that generates a second intermediate signal from a received electrical signal by means of either or both of a fixed type (Boxcar) and a fixed type (Hamming). In addition, the comparison and synthesis processing block 008 is a synthesizing unit that synthesizes the first intermediate signal and the second intermediate signal through a comparison therebetween. Here, note that the contents of individual processing of the DCMP to which spatial smoothing is applied, the fixed type (Boxcar), and the fixed type (Hamming) have already been described, and hence a detailed explanation thereof is omitted.

(Operation of the Ultrasonic Apparatus)

When a position (transmission focus) at which an ultrasonic wave is transmitted is set, the setting information is sent from the system control unit 004 to the transmission circuit system 003. The transmission circuit system 003 transmits an electrical signal for driving the plurality of transducers 002 in the ultrasonic probe 001 after determining a time delay and an intensity based on the information. This electrical signal is converted into a displacement in each of the transducers 002, so that it propagates through the interior of the specimen as an ultrasonic wave. The ultrasonic wave transmitted in this manner returns to the transducers 002 as an ultrasonic signal that has been scattered about and reflected due to an acoustic property in the specimen. The ultrasonic signal is converted into a plurality of received electrical signals by means of these plurality of transducers 002 each operating as an ultrasonic to electrical transducer. These plurality of received electrical signals are inputted to the receiving circuit system 005. In accordance with the information given from the system control unit 004, the receiving circuit system 005 performs an adjustment of the rate of signal amplification according to depth, an adjustment of the time delay according to a received position, and so on. After such adjustments have been made, the received electrical signals are inputted to the fixed signal processing block 006 and the adaptive signal processing block 007.

The fixed signal processing block 006 generates a signal power P2 (second intermediate signal) from the plurality of received electrical signals by the use of a predetermined fixed weight vector, and outputs it to the comparison and synthesis processing block 008. Here, note that the fixed weight vector does not change according to the received electrical signals, but may be changed according to depth, signal frequency, and the kind of the ultrasonic probe.

The adaptive signal processing block 007 determines the weight vector adaptively from a sub-correlation matrix obtained by spatial smoothing and an observation direction designated, and generates a signal power P1 (first intermediate signal) from the plurality of received electrical signals by the use of the weight vector thus determined. Here, note that a vector for designating the observation direction need not be specified in particular if the time delay processing of the signals is completed in the receiving circuit system 005. However, in the case of designating the observation direction separately, information is transmitted from the system control unit 004. The signal power P1 calculated in this manner is outputted to the comparison and synthesis processing block 008.

The comparison and synthesis processing block 008 carries out processing based on the two signal powers P1, P2 inputted. This processing will be described later. A signal outputted from the comparison and synthesis processing block 008 is inputted to the image processing system 009, where various kinds of image processing such as rearrangement according to scanning regions, smoothing, and edge enhancement, etc., is performed, and a tomographic image or a three-dimensional image is generated. The image is displayed on the image display device 010. The above is a main flow of signals.

(Comparison and Synthesis Processing)

Figure 2:
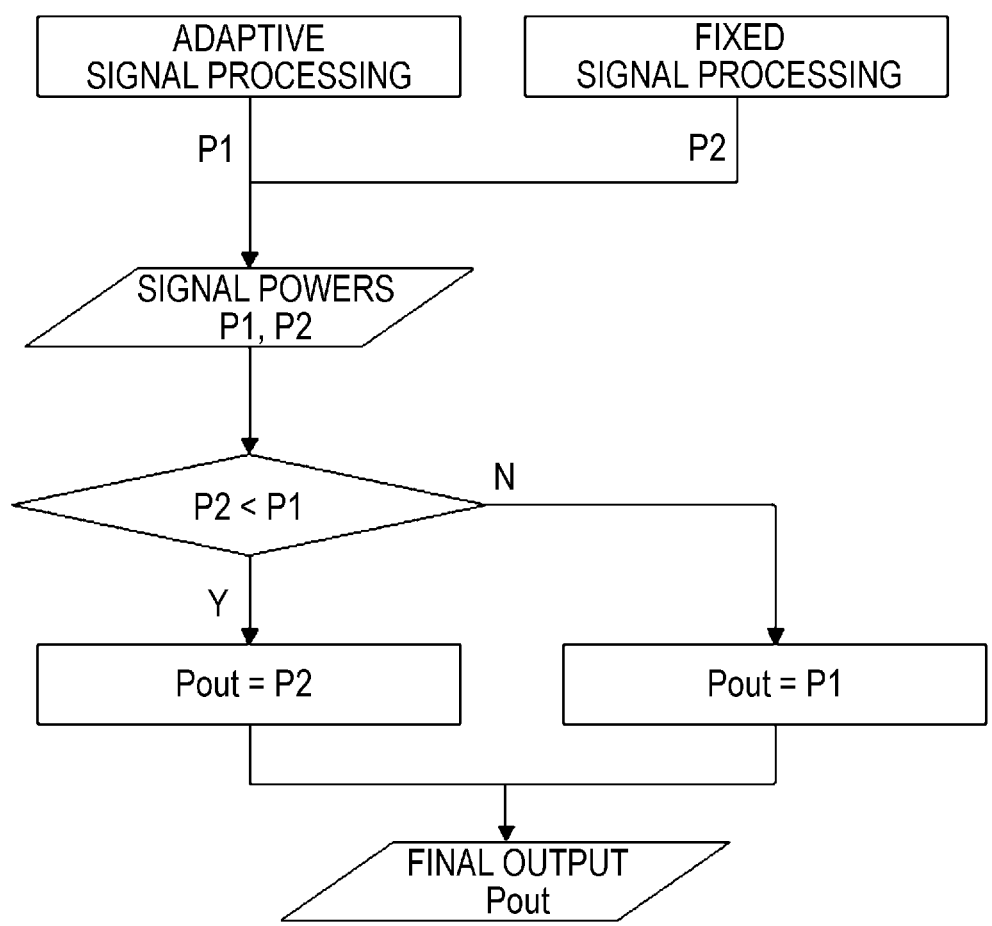
FIG. 2 is a view showing comparison and synthesis processing of a first embodiment.

Next, the processing in the comparison and synthesis processing block 008 will be described by using FIG. 2. The comparison and synthesis processing block 008 makes a comparison between the two signal powers, by using as its inputs, the signal power P1 calculated by the adaptive signal processing and the signal power P2 calculated by the fixed signal processing. In the case where the signal power P2 is smaller than the signal power P1 (i.e., in cases where the signal power due to the fixed type signal processing is smaller than that due to the adaptive type signal processing), the comparison and synthesis processing block 008 adopts and outputs P2 which is the result of the fixed type signal processing. In cases other than this, the comparison and synthesis processing block 008 adopts and outputs P1 which is the result of the adaptive type signal processing.

Figure 3A:
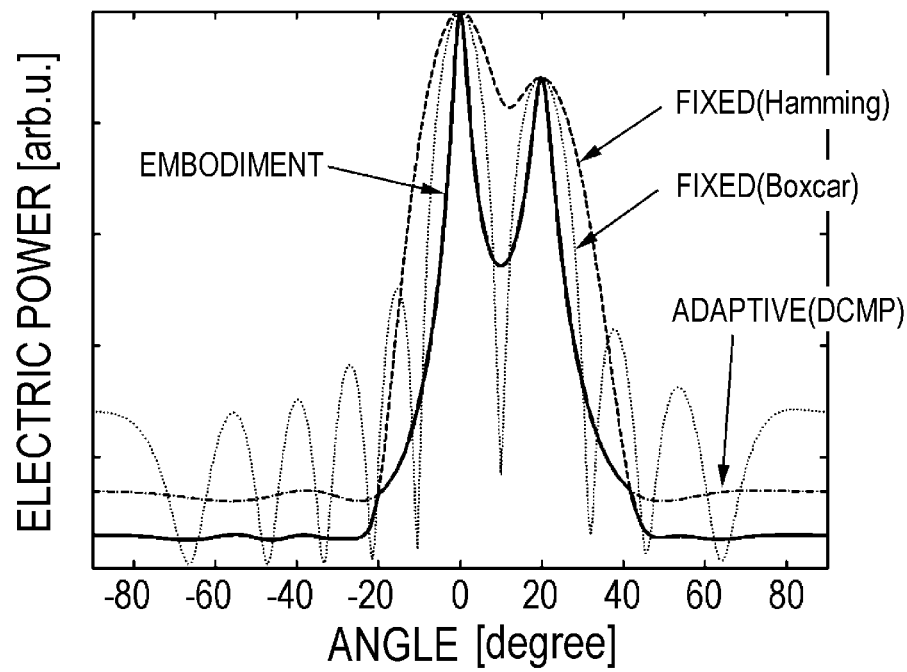
FIG. 3A and FIG. 3B are views explaining the effect of the first embodiment.
Figure 3B:
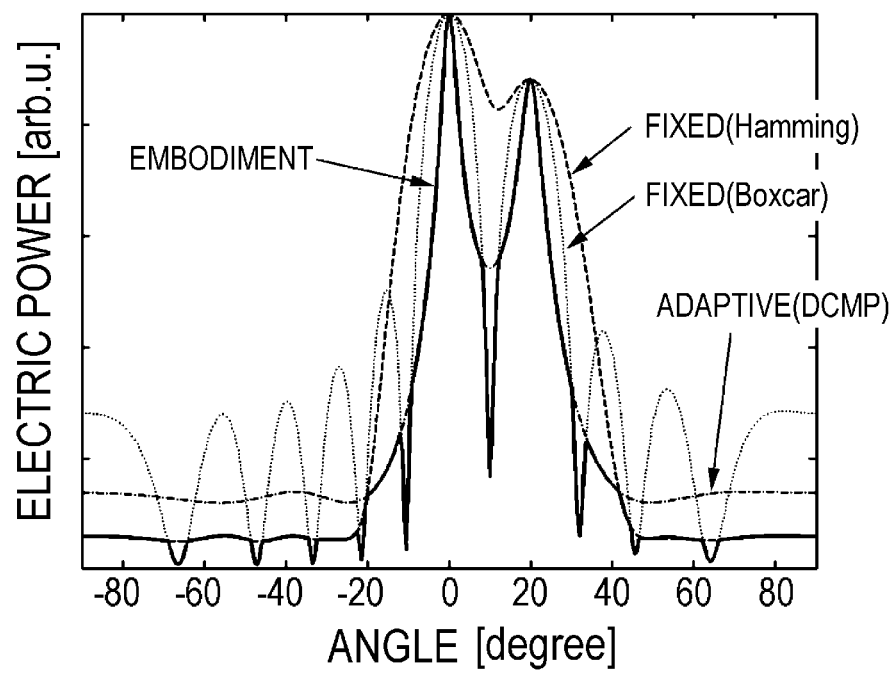
Figure 8A:
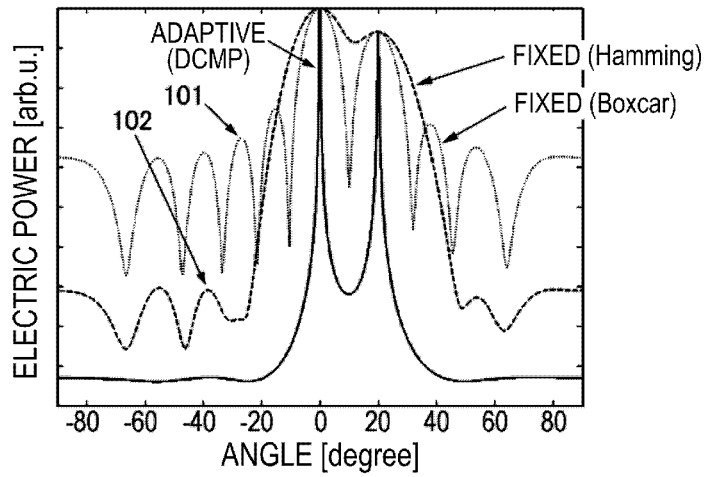
FIG. 8A through FIG. 8C are views showing examples of adaptive processing and fixed processing.
Figure 8B:
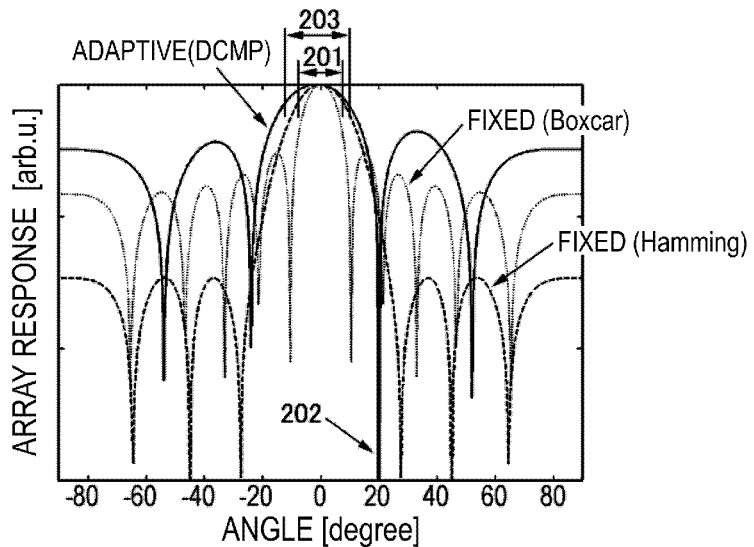
Figure 8C:
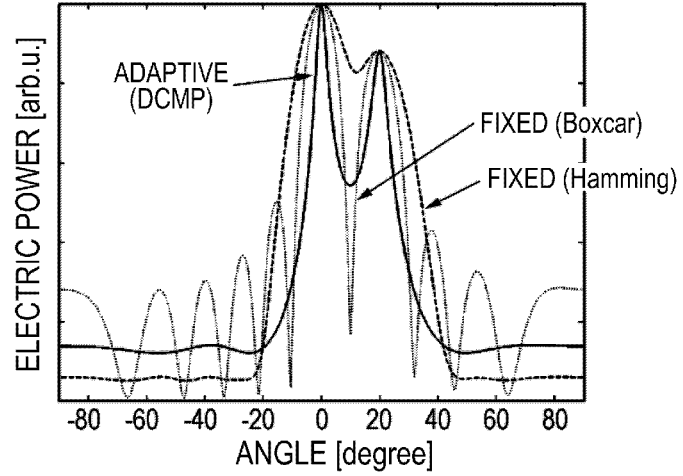

FIG. 3A shows that the signal obtained by the comparison and synthesis processing of this embodiment is added to that of FIG. 8C. In FIG. 3A, a signal power of the "ADAPTIVE (DCMP)" corresponds to the first intermediate signal P1, and a signal power of the "FIXED (Hamming)" corresponds to the second intermediate signal P2. In the comparison and synthesis processing, in cases where the signal power of the FIXED (Hamming) is smaller than the signal power of the ADAPTIVE (DCMP), the signal power of the FIXED (Hamming) is outputted, and in cases other than this, the signal power of the ADAPTIVE (DCMP) is outputted. As a result, an output signal as indicated by a thick line in FIG. 3A is obtained. In addition, FIG. 3B shows the results of processing in which two signals, i.e., the signal power of the "FIXED (Hamming)" and the signal power of the "FIXED (Boxcar)", are each made the second intermediate signal P2, and the signal power of the "ADAPTIVE (DCMP)" is made the first intermediate signal P1. That is, a minimum electric power is outputted among those of the FIXED (Hamming), the FIXED (Boxcar), and the ADAPTIVE (DCMP).

Figure 4A:
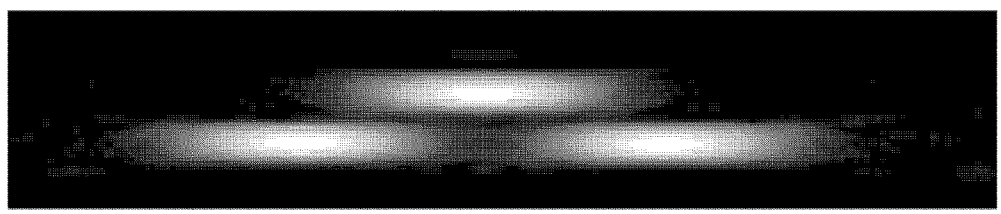
FIG. 4A through FIG. 4C are views showing a tomographic image simulation for explaining the effect of the first embodiment.
Figure 4B:
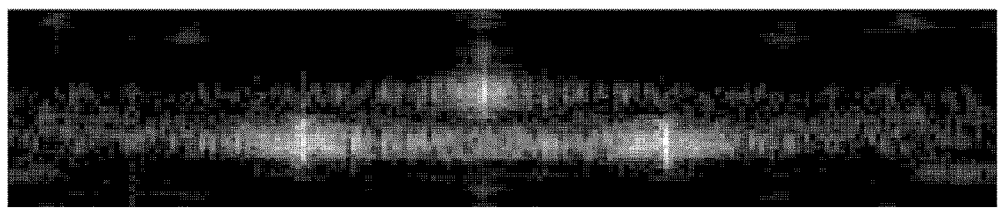
Figure 4C:
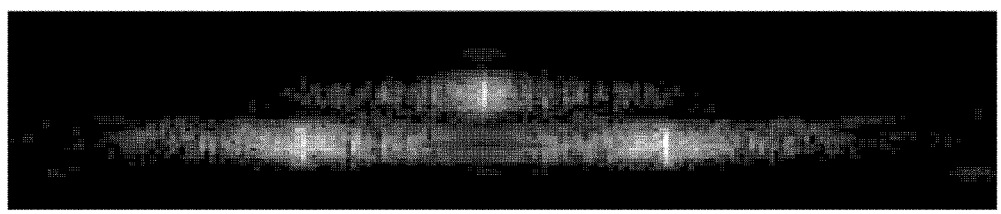

FIG. 4A through FIG. 4C show a tomographic image simulation in the case of visualizing a point target. FIG. 4A plots the output P2 of the fixed signal processing block 006 as it is; FIG. 4B plots the output P1 of the adaptive signal processing block 007 as it is; and FIG. 4C plots the output Pout of the comparison and synthesis processing block 008. As can be seen form FIG. 4A through FIG. 4C, by performing the signal processing of this embodiment, the noise appearing to be caused by side lobes existing around the point target can also be suppressed while holding the spatial resolution of the point target at a high level.

As described above, in this embodiment, by selecting between the signal powers calculated by two kinds of signal processing, i.e., of a fixed type and an adaptive type, it is possible to obtain an image with a high spatial resolution while suppressing the reduction of the contrast ratio thereof.

Here, note that in this embodiment, imaging is carried out by transmitting an ultrasonic wave and using a reflected wave thereof. However, if the transmission of an ultrasonic wave is changed to the transmission of optical energy of a specific wavelength, similar received signal processing can be performed to an ultrasonic wave produced due to a photoacoustic effect, and in this case, too, it is possible to obtain an image having a high spatial resolution with the reduction of the contrast ratio thereof being suppressed.

Second Embodiment

Figure 5A:
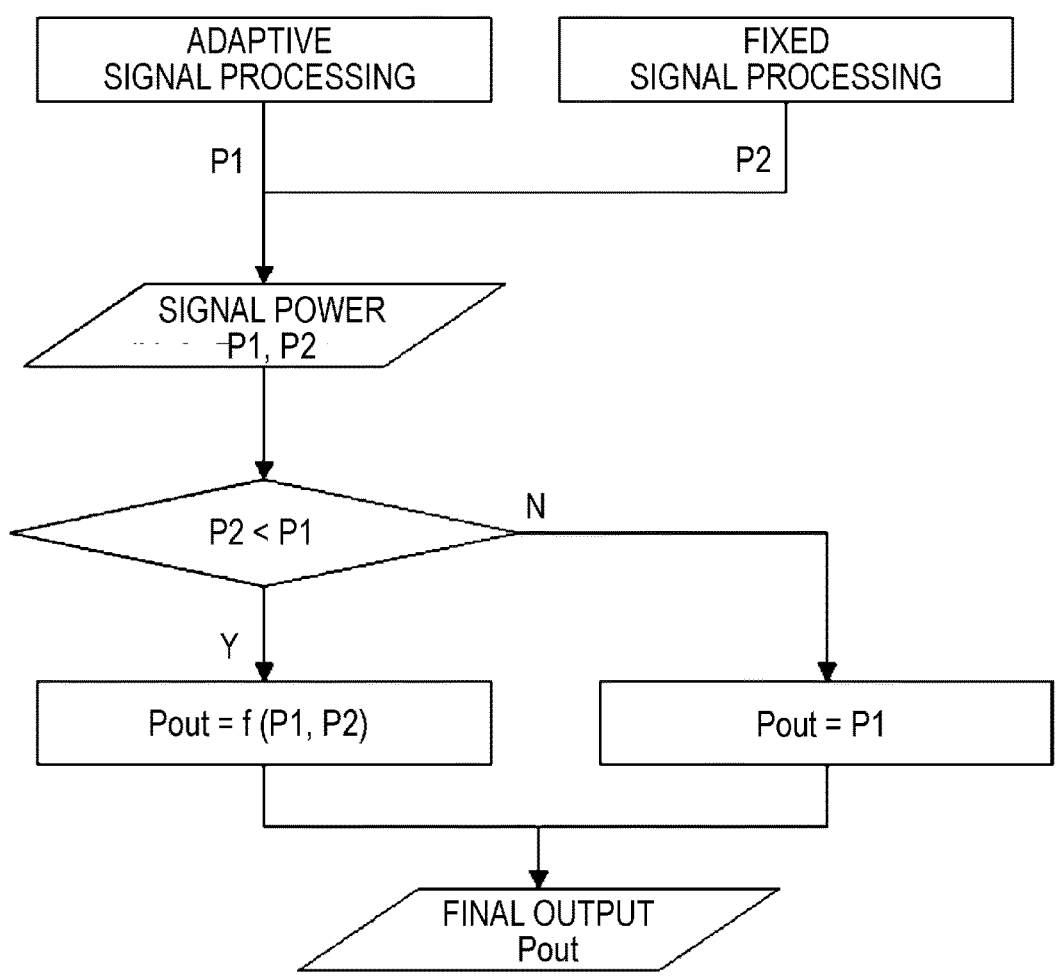
FIG. 5A is a view showing comparison and synthesis processing of a second embodiment.

Next, a second embodiment of the present invention will be described. Although in this second embodiment, it is possible to use the system of FIG. 1 shown in the first embodiment, different processing is carried out in the comparison and synthesis processing block 008. FIG. 5A illustrates that processing. The comparison and synthesis processing block 008 makes a comparison between two signal powers, by using as its inputs, a signal power P1 calculated by adaptive type signal processing and a signal power P2 calculated by fixed type signal processing. In the case where the signal power P2 is smaller than the signal power P1, i.e., in cases where the signal power due to the fixed type signal processing is smaller than that due to the adaptive type signal processing, the comparison and synthesis processing block 008 generates an output by synthesizing the signal power P1 and the signal power P2. In cases other than that, the comparison and synthesis processing block 008 adopts and outputs P1 which is the result of the adaptive type signal processing. The techniques of synthesizing the signal power P1 and the signal power P2 can use, for example, a simple mean, a geometric mean, or the like. Also, the synthesis techniques may use a weighted mean, a weighted geometric mean or the like which can be calculated by using a coefficient α transmitted from the system control unit 004. A synthesized signal Pout=f(P1, P2) obtained by each synthetic technique can be represented as follows.

Simple mean: $Pout = \dfrac{P1 + P2}{2}$

Geometric mean: $Pout = \sqrt{P1 \times P2}$

Weighted mean: $Pout = (1 - \alpha)P1 + \alpha\ P2$

Weighted geometric mean: $Pout = P1^{(1-\alpha)} \times P2^{\alpha}$

Figure 5B:
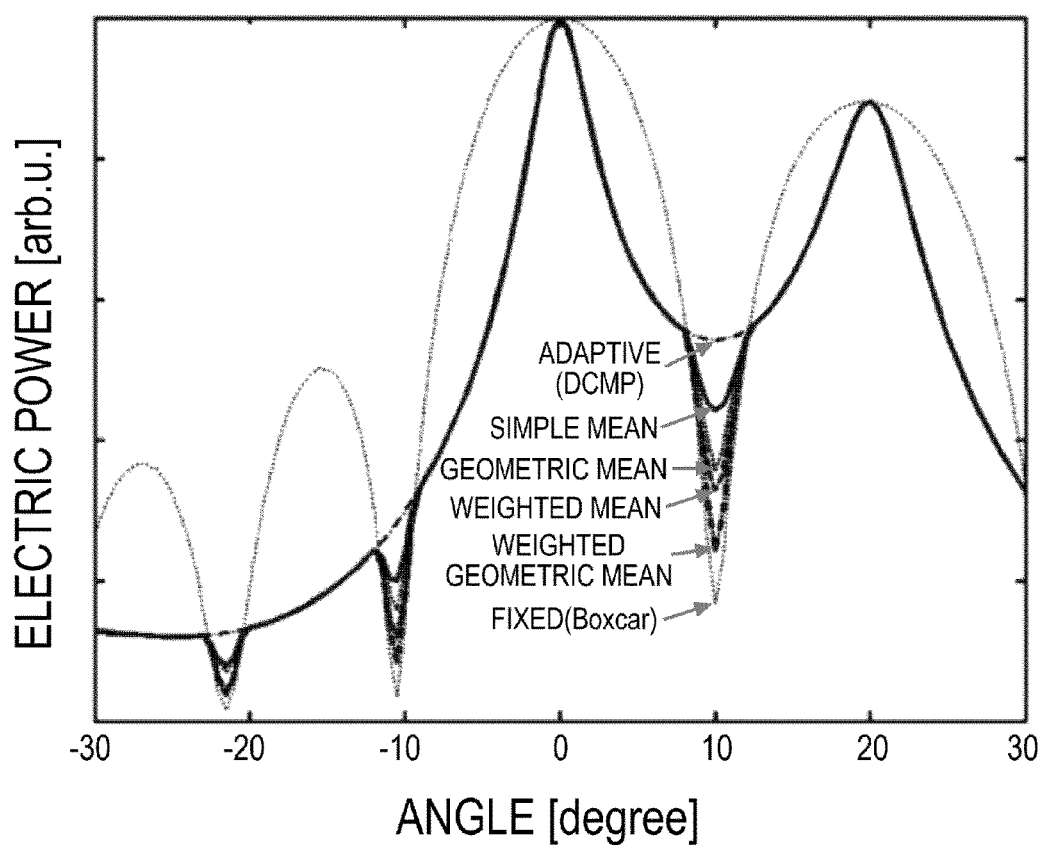
FIG. 5B is a view explaining the effect thereof.

FIG. 5B shows the processing results of the individual techniques. Here, note that the coefficient α was set to 0. Thus, by synthesizing P1 and P2 to generate the output Pout, it is possible to suppress an abrupt change of the signal power at a location where the output Pout is switched over between the adaptive type and the other type. By so doing, it is possible to prevent an unnatural change of brightness at the time of displaying an image from being emphasized, thereby making it possible to provide a clearer and more legible image. Although the coefficient α may use a preset value, an operator is able to change it during an image is displayed.

Third Embodiment

Next, a third embodiment of the present invention will be described. This embodiment can also be achieved by the system of FIG. 1 used in the first embodiment. However, signals exchanged between processing blocks in this third embodiment are different those in the first embodiment, so the operations of the fixed signal processing block 006, the adaptive signal processing block 007, and the comparison and synthesis processing block 008 will again be explained by using FIG. 1.

Received electrical signals are inputted from the receiving circuit system 005 to the fixed signal processing block 006 and the adaptive signal processing block 007, similar to the first embodiment. The fixed signal processing block 006 generates an amplitude signal S2 (second intermediate signal) from the plurality of received electrical signals by the use of a predetermined fixed weight vector, and outputs it to the comparison and synthesis processing block 008. Here, note that the fixed weight vector does not change according to the received electrical signals, but may be changed according to depth, signal frequency, and the kind of the ultrasonic probe. The adaptive signal processing block 007 determines the weight vector adaptively from a sub-correlation matrix obtained by spatial smoothing and an observation direction designated, and generates an amplitude signal S1 (first intermediate signal) from the plurality of received electrical signals by the use of the weight vector thus determined. A method of designating the observation direction is the same as that of the first embodiment. The amplitude signal S1 is outputted to the comparison and synthesis processing block 008.

Figure 6:
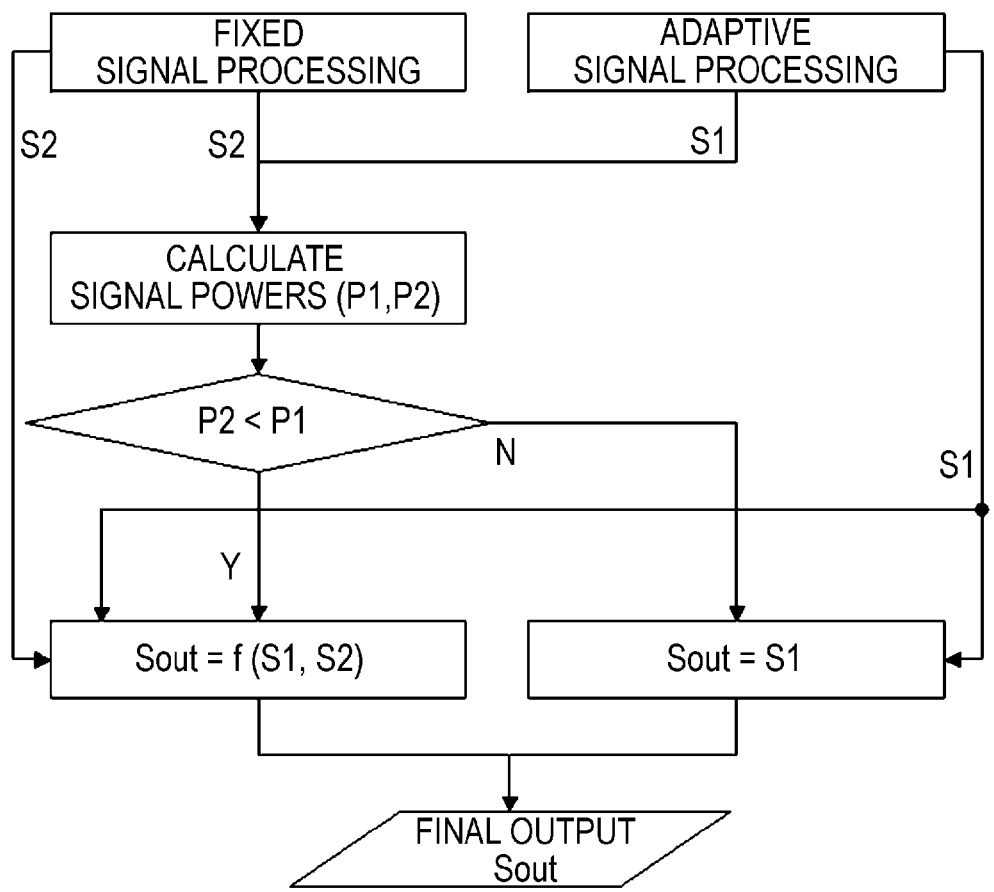
FIG. 6 is a view showing comparison and synthesis processing of a third embodiment.

Now, the processing in the comparison and synthesis processing block 008 will be described by using FIG. 6. The comparison and synthesis processing block 008 calculates two signal powers P1, P2 by using, as its inputs, the amplitude signal S1 calculated by adaptive type signal processing and the amplitude signal S2 calculated by fixed type signal processing. The comparison and synthesis processing block 008 compares these signal powers P1, P2 with each other. In the case where the signal power P2 is smaller than the signal power P1, i.e., in cases where the signal power due to the fixed type signal processing is smaller than that due to the adaptive type signal processing, the comparison and synthesis processing block 008 generates an output by synthesizing S2 which is the result of the fixed type signal processing, and S1 which is the result of the adaptive type signal processing. In cases other than that, the comparison and synthesis processing block 008 adopts and outputs S1 which is the result of the adaptive type signal processing. The synthesis technique can use a simple mean, a geometric mean, a weighted mean, a weighted geometric mean, or the like, similar to the second embodiment. In this embodiment, an amplitude signal can be outputted instead of a signal power, so it becomes possible to carry out, as subsequent processing, processing that needs phase information such as finding the speed of a supersonic wave in a specimen by means of Doppler processing.

Fourth Embodiment

Next, a fourth embodiment of the present invention will be described. Although this fourth embodiment can also be carried out by the system of FIG. 1, the processing in the comparison and synthesis processing block is different from each other, so the following explanation will be given while focusing on different portions. Here, note that signal powers P1, P2 are inputted to the comparison and synthesis processing block in this embodiment.

Figure 7A:
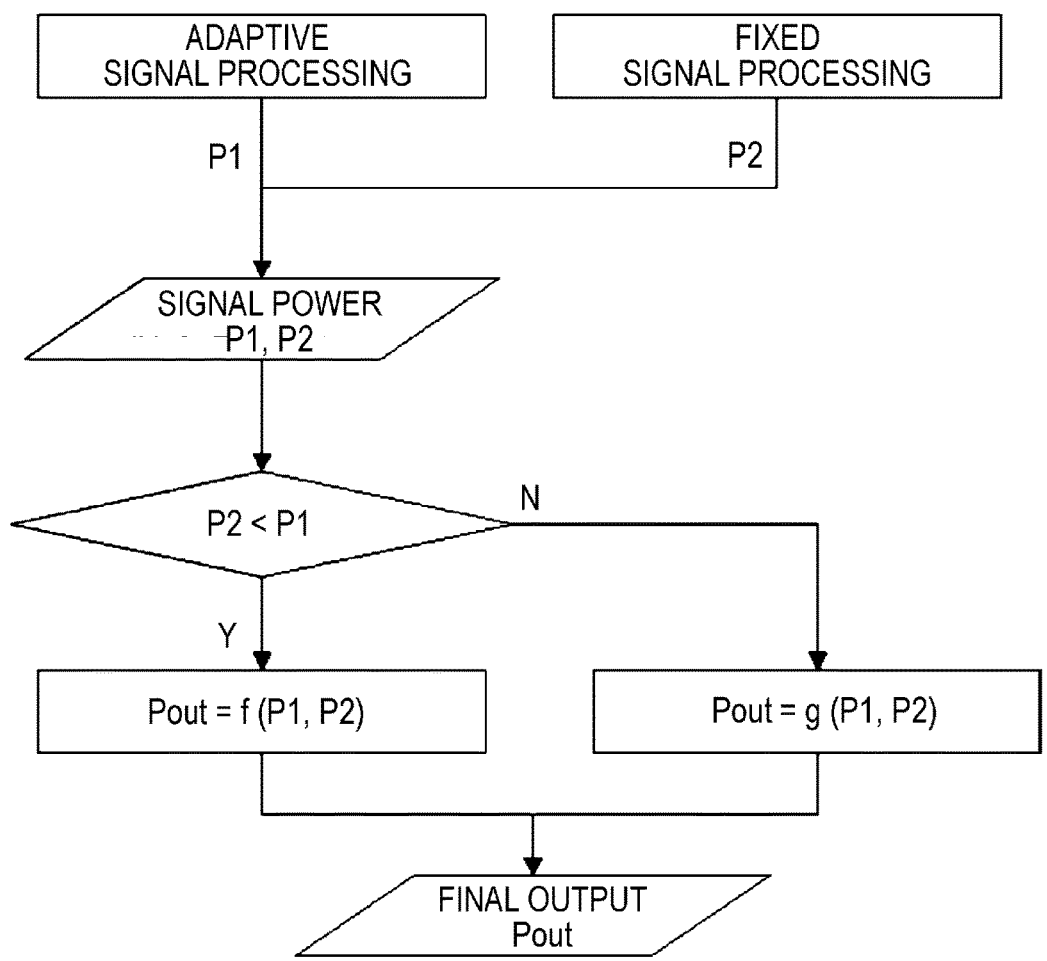
FIG. 7A is a view showing comparison and synthesis processing of a fourth embodiment.

FIG. 7A is a view explaining the processing in the comparison and synthesis processing block of this embodiment. The comparison and synthesis processing block 008 makes a comparison between two signal powers, by using as its inputs, the signal power P1 calculated by adaptive type signal processing and the signal power P2 calculated by fixed type signal processing. In the case where the signal power P2 is smaller than the signal power P1, i.e., in cases where the signal power due to the fixed type signal processing is smaller than that due to the adaptive type signal processing, the comparison and synthesis processing block 008 synthesizes the signal power P1 and the signal power P2 by using a first function f(P1, P2). In cases other than that, the comparison and synthesis processing block 008 synthesizes the signal power P1 and the signal power P2 by using a second function g(P1, P2). The functions f and g can use a simple mean, a geometric mean, a weighted mean, a weighted geometric mean, or the like. However, the functions f and g are mutually different from each other in the synthesis formula and/or the coefficient of weight.

FIG. 7B shows the result of the processing in this embodiment. It is the processing result of DCMP in which the smaller one of the signal powers in a Boxcar window and a Hamming window is inputted as a signal power from a fixed type, and spatial smoothing is applied to a signal power from an adaptive type. In addition, FIG. 7B shows the results of a weighted mean and a weighted geometric mean. Here, note that a value of 0.1 is used as the value of the coefficient α (for the function f) in cases where the signal power of the fixed type is smaller, and a value of 0.8 is used as the value of the coefficient α (for the function g) in cases where the signal power of the adaptive type is smaller. That is, the function f is a synthesis technique in which the weight of the signal power P2 of the fixed type is larger, and the function g is a synthesis technique in which the weight of the signal power P1 of the adaptive type is larger. In cases where the signal power of the fixed type is smaller, by performing the processing of this embodiment, there is obtained an effect that an increase in the side lobe level, which would otherwise be caused due to spatial smoothing, can be suppressed, thereby keeping the contrast ratio of an image high. Moreover, by synthesizing the signal powers, an unnatural change of brightness is prevented from being emphasized. In addition, also in cases where the signal power of the adaptive type is smaller, by performing the synthesis of P1 and P2, it becomes possible to suppress an abrupt change of the signal power at a location where the formula for an output Pout is switched over. Further, adaptive signal processing enhances spatial resolution, so even a reflector in a specimen having a spread on a screen in the case of fixed signal processing, when subjected to adaptive signal processing for example, may become a bright spot of one pixel on a screen display. Even in such a case, by synthesizing the two kinds of signal powers in a portion where the signal power of the adaptive type is smaller than the signal power of the fixed type, as in this embodiment, spatial resolution can be degraded a little, thereby making it possible to improve visibility.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An ultrasonic apparatus which acquires specimen information by receiving an ultrasonic wave from a specimen, said apparatus comprising:

a plurality of transducers that receive ultrasonic waves and convert them into respective received electrical signals;

an adaptive signal processing unit that generates a first intermediate signal by an adaptive signal processing with the use of a plurality of received electrical signals obtained from said plurality of transducers;

a fixed signal processing unit that generates a second intermediate signal with the use of the plurality of received electrical signals and a predetermined weighting coefficient; and a processing unit that generates an output signal to be used for acquisition of the specimen information based on the first intermediate signal and the second intermediate signal, wherein, when intensity of the second intermediate signal is smaller than intensity of the first intermediate signal, said processing unit outputs as the output signal, one of (a) the second intermediate signal and (b) a signal which is generated by using the first intermediate signal and the second intermediate signal and whose intensity is smaller than the intensity of the first intermediate signal, and wherein, when the intensity of the second intermediate signal is not smaller than the intensity of the first intermediate signal, said processing unit outputs as the output signal, one of (c) the first intermediate signal and (d) a signal which is generated by using the first intermediate signal and the second intermediate signal and whose intensity is smaller than the intensity of the second intermediate signal.

2. An ultrasonic apparatus according to claim 1, wherein, when the intensity of the second intermediate signal is smaller than the intensity of the first intermediate signal, said processing unit outputs the second intermediate signal, and wherein, when the intensity of the second intermediate signal is not smaller than the intensity of the first intermediate signal, said processing unit outputs the first intermediate signal.

3. An ultrasonic apparatus according to claim 1, wherein, when the intensity of the second intermediate signal is smaller than the intensity of the first intermediate signal, said processing unit synthesizes the first intermediate signal and the second intermediate signal and outputs the synthesized signal, and wherein, when the intensity of the second intermediate signal is not smaller than the intensity of the first intermediate signal, said processing unit outputs the first intermediate signal.

4. An ultrasonic apparatus according to claim 1, wherein, when the intensity of the second intermediate signal is smaller than the intensity of the first intermediate signal, said processing unit synthesizes the first intermediate signal and the second intermediate signal by using a first function and outputs the synthesized signal, and wherein, when the intensity of the second intermediate signal is not smaller than the intensity of the first intermediate signal, said processing unit synthesizes the first intermediate signal and the second intermediate signal by using a second function being different from the first function and outputs the synthesized signal.

5. An ultrasonic apparatus according to claim 4, wherein the first function is a synthesis technique in which a weight for the second intermediate signal is larger than a weight for the first intermediate signal, and the second function is a synthesis technique in which a weight for the first intermediate signal is larger than a weight for the second intermediate signal.

6. An ultrasonic apparatus according to claim 1, wherein said processing unit outputs the output signal having smaller intensity than the second intermediate signal when the intensity of the first intermediate signal is smaller than the intensity of the first intermediate signal.

7. An ultrasonic apparatus according to claim 1, wherein said adaptive signal processing unit performs the adaptive signal processing by using a weighting coefficient which varies adaptively according to the plurality of received electrical signals.

8. An ultrasonic apparatus according to claim 1, wherein said adaptive signal processing unit performs the adaptive signal processing by applying spatial smoothing.

9. An ultrasonic apparatus according to claim 1, wherein said adaptive signal processing unit processes the plurality of received electrical signals so as to minimize output intensity with sensitivity in a certain direction being fixed.

10. An ultrasonic apparatus according to claim 1, wherein said adaptive signal processing unit obtains a correlative matrix by using the plurality of received electrical signals, determines a weighting coefficient based on a sub-correlation matrix which is obtained by averaging sub-matrices in the correlative matrix, and, performs the adaptive signal processing by using the obtained weighting coefficient.

11. An ultrasonic apparatus according to claim 1, wherein said fixed signal processing unit uses, as the predetermined weighting coefficient, at least one of a weighting coefficient having uniform magnitude and a weighting coefficient obtained from a Hamming window.

12. A method for acquiring specimen information by receiving an ultrasonic wave from a specimen, said method comprising:
generating a first intermediate signal by adaptive signal processing with the use of a plurality of received electrical signals obtained by a plurality of transducers which are configured to receive a plurality of ultrasonic waves and convert them into the plurality of received electrical signals;
generating a second intermediate signal by fixed signal processing with the use of the plurality of received electrical signals and a predetermined weighting coefficient; and
generating an output signal to be used for acquisition of the specimen information based on the first intermediate signal and the second intermediate signal,
wherein, when intensity of the second intermediate signal is smaller than intensity of the first intermediate signal, the output signal outputted in said step of generating the output signal is one of (a) the second intermediate signal and (b) a signal which is generated by using the first intermediate signal and the second intermediate signal and whose intensity is smaller than the intensity of the first intermediate signal, and
wherein, when the intensity of the second intermediate signal is not smaller than the intensity of the first intermediate signal, the output signal outputted in said step of generating the output signal is one of (c) the first intermediate signal and (d) a signal which is generated by using the first intermediate signal and the second intermediate signal and whose which intensity is smaller than the intensity of the second intermediate signal.

13. A method according to claim 12, wherein, when the intensity of the second intermediate signal is smaller than the intensity of the first intermediate signal, said step of generating the output signal includes outputting the second intermediate signal, and
wherein, when the intensity of the second intermediate signal is not smaller than the intensity of the first intermediate signal, said step of generating the output signal includes outputting the first intermediate signal.

14. A method according to claim 12, wherein, when the intensity of the second intermediate signal is smaller than the intensity of the first intermediate signal, said step of generating the output signal includes synthesizing the first intermediate signal and the second intermediate signal and outputting the synthesized signal, and
wherein, when the intensity of the second intermediate signal is not smaller than the intensity of the first intermediate signal, said step of generating the output signal includes outputting the first intermediate signal.

15. A method according to claim 12, wherein, when the intensity of the second intermediate signal is smaller than the intensity of the first intermediate signal, said step of generating the output signal includes synthesizing the first intermediate signal and the second intermediate signal by using a first function and outputting the synthesized signal, and
wherein, when the intensity of the second intermediate signal is not smaller than the intensity of the first intermediate signal, said step of generating the output signal includes synthesizing the first intermediate signal and the second intermediate signal by using a second function that is different from the first function and outputting the synthesized signal.

16. A method according to claim 15, wherein the first function is a synthesis technique in which a weight for the second intermediate signal is larger than a weight for the first intermediate signal, and the second function is a synthesis technique in which a weight for the first intermediate signal is larger than a weight for the second intermediate signal.

17. A method according to claim 12, wherein said step of generating the output signal includes outputting the output signal having smaller intensity than the second intermediate signal when the intensity of the first intermediate signal is smaller than the intensity of the first intermediate signal.

18. A method according to claim 12, wherein said step of generating the first intermediate signal includes performing the adaptive signal processing by using a weighting coefficient which varies adaptively according to the plurality of received electrical signals.

19. A method according to claim 12, wherein said step of generating the first intermediate signal includes performing the adaptive signal processing by applying spatial smoothing.

20. A method according to claim 12, wherein said step of generating the first intermediate signal includes processing the plurality of received electrical signals so as to minimize output intensity with sensitivity in a certain direction being fixed.

21. A method according to claim 12, wherein said step of generating the first intermediate signal includes obtaining a correlative matrix by using the plurality of received electrical signals, determining a weighting coefficient based on a sub-correlation matrix which is obtained by averaging sub-matrices in the correlative matrix, and performing the adaptive signal processing by using the obtained weighting coefficient.

22. A method according to claim 12, wherein said step of generating the second intermediate signal includes using, as the predetermined weighting coefficient, at least one of a weighting coefficient having uniform magnitude and a weighting coefficient obtained from a Hamming window.

23. An ultrasonic apparatus which acquires biological information by receiving an ultrasonic wave from a specimen, said apparatus comprising:
- a plurality of transducers that transmit ultrasonic waves to the specimen and receive ultrasonic waves reflected in the specimen and convert the received ultrasonic waves into respective received electrical signals;
- an adaptive signal processing unit that generates a first intermediate signal by performing an adaptive signal processing with the use of a plurality of received electrical signals obtained from said plurality of transducers;
- a fixed signal processing unit that generates a second intermediate signal with the use of the plurality of received electrical signals and a predetermined weighting coefficient; and
- a unit that generates an output signal to be used for acquisition of the biological information by comparing the first intermediate signal and the second intermediate signal,
- wherein the adaptive signal processing unit generates the first intermediate signal independently from the second intermediate signal, and
- wherein said adaptive signal processing unit obtains a correlative matrix by using the plurality of received electrical signals, determines a weighting coefficient based on a sub-correlation matrix which is obtained by averaging sub-matrices in the correlative matrix, and, performs the adaptive signal processing by using the obtained weighting coefficient.

24. The ultrasonic apparatus according to claim 23, wherein said adaptive signal processing unit processes the plurality of received electrical signals so as to minimize output intensity with sensitivity in a certain direction being fixed.

25. A method for acquiring biological information by receiving an ultrasonic wave from a specimen, said method comprising the steps of:
- transmitting ultrasonic waves to the specimen;
- receiving ultrasonic waves reflecting in the specimen and converting the received ultrasonic waves into received electrical signals by means of a plurality of transducers;
- generating a first intermediate signal by performing an adaptive signal processing with the use of a plurality of received electrical signals obtained from the plurality of transducers;
- generating a second intermediate signal with the use of the plurality of received electrical signals and a predetermined weighting coefficient; and
- generating an output signal to be used for acquisition of the biological information by comparing the first intermediate signal and the second intermediate signal,
- wherein, in generating the first intermediate signal, the first intermediate signal is generated independently from the second intermediate signal, and
- wherein said step of generating the first intermediate signal includes obtaining a correlative matrix by using the plurality of received electrical signals, determining a weighting coefficient based on a sub-correlation matrix which is obtained by averaging sub-matrices in the correlative matrix, and performing the adaptive signal processing by using the obtained weighting coefficient.

26. The method according to claim 25, wherein said step of generating the first intermediate signal includes processing the plurality of received electrical signals so as to minimize output intensity with sensitivity in a certain direction being fixed.

* * * * *